(12) United States Patent
Kumar et al.

(10) Patent No.: US 6,195,574 B1
(45) Date of Patent: Feb. 27, 2001

(54) MONITORING CONSTITUENTS OF AN ANIMAL ORGAN USING DISCRETE RADIATION

(75) Inventors: Gitesh Kumar, Norwalk; Joseph L. DiCesare, Redding, both of CT (US)

(73) Assignee: PerkinElmer Instruments LLC, Norwalk, CT (US)

( * ) Notice: Subject to any disclaimer, the term of this patent is extended or adjusted under 35 U.S.C. 154(b) by 0 days.

(21) Appl. No.: 09/385,242

(22) Filed: Aug. 28, 1999

Related U.S. Application Data

(60) Provisional application No. 60/099,097, filed on Sep. 4, 1998.

(51) Int. Cl.[7] .................................................. A61B 5/00
(52) U.S. Cl. ............................................ 600/323; 600/310
(58) Field of Search .................................... 600/310, 322, 600/323, 330, 336, 473; 250/339.01, 339.07, 341.1; 356/39–41, 317, 318, 319, 323

(56) References Cited

U.S. PATENT DOCUMENTS

| | | | |
|---|---|---|---|
| 5,122,974 | * | 6/1992 | Chance .................................. 600/323 |
| 5,386,827 | * | 2/1995 | Chance et al. ........................ 600/310 |
| 5,664,574 | * | 9/1997 | Chance .................................. 600/473 |

* cited by examiner

*Primary Examiner*—Eric F. Winakur
(74) *Attorney, Agent, or Firm*—St. Onge Steward Johnston & Reens LLC

(57) ABSTRACT

Constituents such as oxy- and deoxy-hemoglobin are monitored non-invasively in an animal organ such as a brain with a spectrometric instrument by passing radiation through the organ. An input beam has a plurality of discrete wavelengths modulated with radio frequency. Output radiation is received by a detector from which output amplitude and output phase are determined for each wavelength. Absorption coefficient is computed from the amplitude and phase, and concentrations of constituents are thereby calculated.

19 Claims, 10 Drawing Sheets

MONITORING CONSTITUENTS OF AN ANIMAL ORGAN USING DISCRETE RADIATION

This application claims the benefit of now abandoned provisional application Ser. No. 60/099,097 filed Sept. 4, 1998. This invention relates to monitoring constituents in an animal organ, particularly oxygenated and deoxygenated hemoglobin in a brain.

BACKGROUND

There has been a desire for an instrument to monitor constituents in an animal or human organ non-invasively. A particular example is monitoring of oxygen level in the brain which is particularly important, for example during surgery, where a significant number of patients come out of the anesthesia with various degrees of and sometimes permanent brain function deficiency. It is believed that in a significant portion of such cases, lack of sufficient oxygen to the brain is the cause of such deficiencies. Thus, the ability to accurately monitor oxygen level in the brain directly, rather than through indirect methods such as a pulse oximeter placed on another portion of the body, would have obvious advantages including non-invasiveness, immediate and timely results, and relative simplicity. Techniques to achieve such monitoring have involved passing near-infrared radiation through a cranium and analyzing the modified output radiation.

One known method is to pass radiation having several discrete wavelengths from laser diodes equal in number to the number of constituents to be measured, for example two wavelengths for oxygenated and deoxygenated hemoglobin. The radiation is modulated with radio frequency. The output modified by the brain is used to calculate changes in amplitude and phase which lead to determination of absorption coefficients at the different wavelengths. Simultaneous equations with these coefficients determine concentrations of the constituents of interest and the oxygen saturation which is the percentage of oxygenated to total hemoglobin.

Another method is to utilize continuous-wave radiation, in which output from a detector on a cranium is spectrally analyzed to yield oxygen saturation. Although a full spectrum is used, the analysis is based on modeling with either a small number of wavelengths or a few known constituents such as the oxy and deoxy hemoglobin and water.

Any such monitoring encounters difficulties resulting from the biological complexities of an organ such as a brain, compared with spectrometric instrumentation that ordinarily analyzes fluids that are readily probed, contained or flowing in a tube suitable for the instrument. Geometries of different subjects vary considerably and variations occur even within an individual. Further, tissues are not uniform. The radiation is scattered so that a path is not well defined. Signal to noise ratios for infrared radiation through solid material are generally low. Current methods for monitoring of craniums depend on theoretical or mathematical models that may be oversimplified or inaccurate. Thus there is a need for better accuracy and reproducibility.

Consequently, an object of the invention is to provide a novel method and means for monitoring constituents in an animal organ non-invasively, particularly oxygenated and deoxygenated hemoglobin in a brain.

SUMMARY

The foregoing and other objects are achieved, at least in part, by monitoring one or more selected constituents in an animal organ with a spectrometric instrument that includes a source of an input beam of discrete radiation and a radiation detector receptive of such radiation to generate representative signal data. The discrete radiation is formed of a plurality of discrete wavelength components in an infrared spectral range that includes absorbance wavelengths of the selected constituents and one or more additional constituents in the organ. Each wavelength component has a predetermined input amplitude and is modulated with a radio frequency signal having a predetermined input phase. The plurality of wavelength components is at least equal in number to the total number of constituents.

The input beam is directed into an animal organ such that the radiation is modified by the constituents. The detector is positioned so as to be receptive of the modified radiation from an exit site from the organ, and generates a corresponding output signal for each wavelength component. From each output signal, an output amplitude and an output phase are determined for each wavelength component. An absorption coefficient is computed for each wavelength component from the input amplitude, the output amplitude, the input phase and the output phase, utilizing respective equations relating phase, amplitude, absorption coefficient and scattering coefficient. Concentration of each of the selected constituents is calculated from a plurality of simultaneous equations at least equal to the total number of constituents, each equation being for a wavelength component relating absorption coefficient to concentrations of all of the constituents proportionately with respective predetermined extinction coefficients. These procedures are particularly advantageous for selected constituents comprising oxygenated hemoglobin and deoxygenated hemoglobin, with the additional constituents being water, protein and lipid. Oxygen saturation in the blood may be calculated as a ratio of concentration of oxygenated hemoglobin to a total of concentrations of oxygenated and deoxygenated hemoglobin.

In a further aspect, to predetermine each input amplitude and input phase, the input beam is passed through a neutral density filter to the radiation detector so as to generate a corresponding reference signal for each wavelength component, the filter having a predetermined optical density. From each reference signal, a reference amplitude and a reference phase are determined for each wavelength component, the input phase being equal to the reference phase. The input amplitude is calculated from the reference amplitude and the optical density.

Accuracy may be improved by a correction procedure. An absorption relationship is provided relating total absorption coefficient for the organ to oxygen saturation, specific absorption coefficients and volume fractions respectively for water, tissue matrix, blood, and for constituents of the tissue matrix and the blood. The specific absorption coefficients are predetermined for each wavelength component, and the volume fractions can vary. At least one set of values is selected for the oxygen saturation and the volume fractions. For each set, from these values, and from the specific absorption coefficients, a corresponding organ absorption coefficient is calculated for a selected wavelength component. The calculated organ absorption coefficients are utilized for computing concentrations of oxygenated hemoglobin and deoxygenated hemoglobin from the plurality of simultaneous equations. Oxygen saturations are calculated from the concentrations. The calculated oxygen saturations are compared to the selected values for oxygen saturation to obtain a correction factor which is stored for future application to the measured oxygen saturation to obtain a corrected oxygen saturation.

In another aspect, calibration factors are generated. At least one standardized medium of a non-absorbing material containing scattering matter is provided, the medium having a predetermined scattering coefficient and nil absorption coefficient. Also a standard sample of each of the selected and additional constituents is provided, the standard samples having predetermined concentrations and predetermined extinction coefficients.

The input beam is directed through the medium in a manner similar to an organ to generate an output signal for the medium. From each output signal, a measured phase is determined for the medium for each wavelength. Additionally, a computed phase for each wavelength is computed from the predetermined scattering coefficient using a model equation relating phase to scattering coefficient.

The input beam is further directed into each standard sample so as to generate an output signal for each sample. From each output signal, a measured amplitude is determined for each sample for selected wavelengths. A set of hypothetical concentrations of the sample constituents is derived for hypothetical organs. From these and the predetermined concentrations, a hypothetical absorption coefficient is computed for each wavelength from an absorption equation relating absorption coefficient to concentrations and extinction coefficients. A set of hypothetical scattering coefficients is selected, and from these and the selected scattering coefficients a computed amplitude is computed for each wavelength from a model equation relating amplitude to absorption coefficient and scattering coefficient.

The measured phase and the computed phase are compared for each wavelength to effect phase calibration factors, and the measured amplitude and the computed amplitude are compared for each wavelength to effect amplitude calibration factors. The factors are stored for future application respectively to output phase and output amplitude computed from signal data for an animal organ.

As an alternative to the foregoing calibration procedure, in the manner described above an absorption coefficient is computed from measured phase and the measured amplitude for each wavelength from the model equations relating phase, amplitude, absorption coefficient and scattering coefficient. The computed absorption coefficient and the hypothetical absorption coefficient are compared for each wavelength to effect coefficient calibration factors. The factors are stored for future application to measured absorption coefficients computed from signal data for an animal organ, to effect corrected absorption coefficients that are used in subsequent calculations of concentrations.

DETAILED DESCRIPTION

Figure 1:
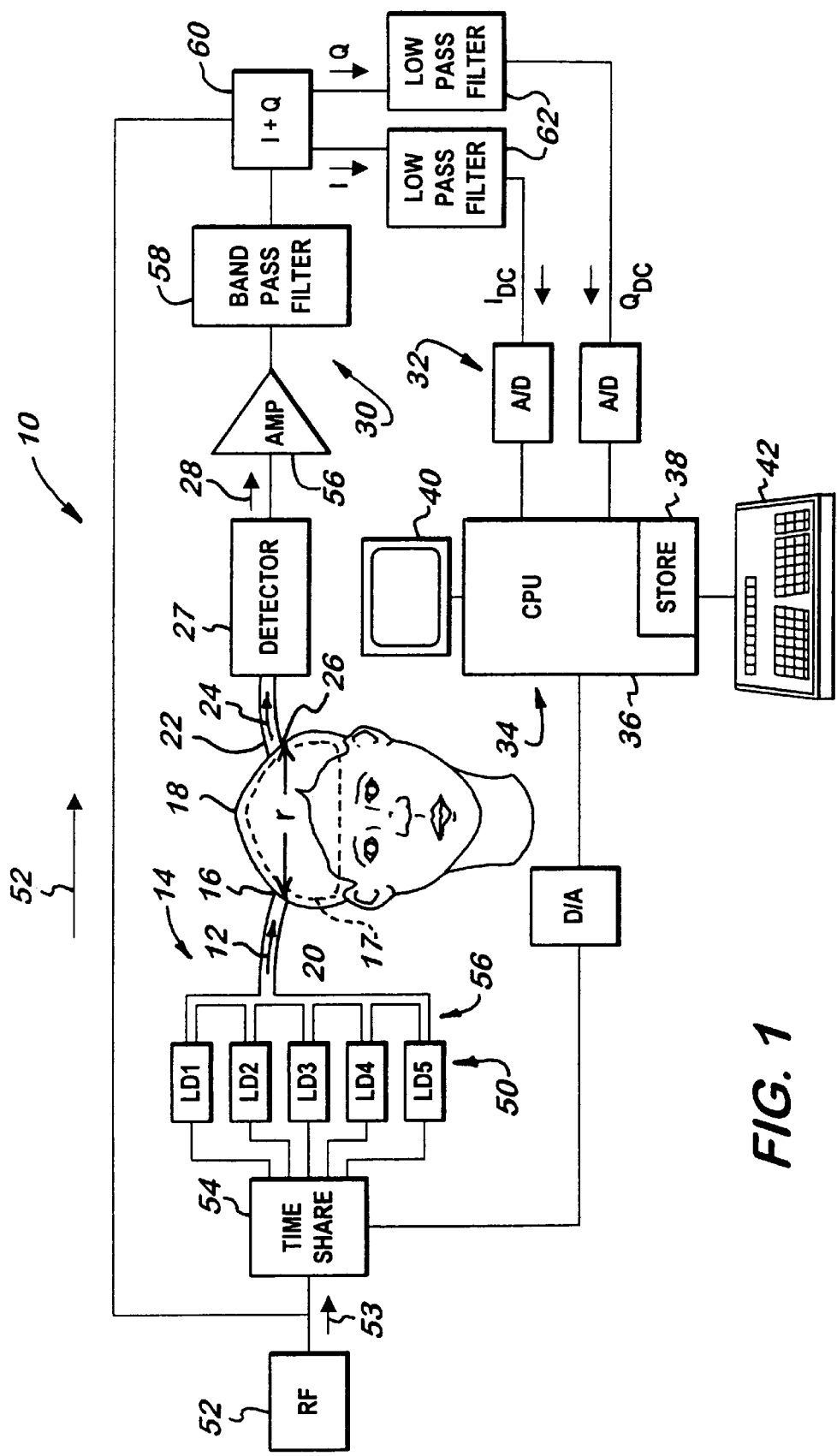
FIG. 1 is a block diagram of an apparatus in accordance with the invention.

A system 10 (FIG. 1) of the invention is directed to passing a beam 12 of infrared radiation from a light source 14 into an input site 16 of a body part of an animal, for example the cranium 18 of a dog or a human being, so as to monitor one or more selected constituents in an organ such as a brain 17. The system is adapted for a living organ that is either in place or temporarily shifted or removed but still connected to the animal during surgery. The constituents may be bimolecular compounds, the system being particularly useful for monitoring oxygenated ("oxy") hemoglobin and deoxygenated ("deoxy") hemoglobin. The body part may be, for example, an external arm, foot, finger or the like, and the organ may be, for example, a brain, colon, liver, gall bladder, etc. The system and method of the invention is especially advantageous where the body part is a cranium which herein means a skull with brain and overlying skin and perhaps hair, and the organ examined is a brain. A fiber optic carrier 20 formed of an optical fiber or preferably a bundle of fibers, e.g. 6 mm diameter, is convenient for conveying the input beam through a light probe to the cranium or other organ which modifies the radiation by absorption and scattering. Alternatively, the input beam may be focused on the cranium directly without a fiber.

A second, similar fiber carrier 22 may be used to entrain the modified radiation 24 exiting the cranium from a suitable point or site 26, for example about 3–4 cm from the input site. The second fiber carrier conveys the modified radiation to a radiation detector 27 to generate corresponding output signals 28 representative of the modified radiation. Alternatively the detector may be positioned proximate the skull without a second fiber carrier, or one or more lenses may pass the radiation from the skull to the detector. The signals are treated by electronic circuitry 30 to effect further signals that are fed through analog/digital (A/D) converters 32 to a computer 34. Alternatively the signals may themselves be treated by computer toward the same result. The computer may be a standard PC or a dedicated processor, typically including a data processor (CPU) 36, disk and RAM storage 38, a monitor 40 for display and a keyboard 42 for operator input.

The spectral range is selected for suitability of the radiation passing through the cranium or other organ with sufficient attenuation by absorption by the selected constituents without excessive interference by other constituents. Oxy and deoxy hemoglobin molecules have broad absorption peaks at about 920 nm and 760 nm which are separated from a strong water peak at about 975 nm. For these peaks it was determined that a spectral range of about 700 nm to 1100 nm is suitable for hemoglobin. Other examples for monitoring or measurement are cytochrome-$aa_3$ oxidase at approximately 840 nm, and other forms of hemoglobin such as carboxy-hemoglobin.

Figure 2:
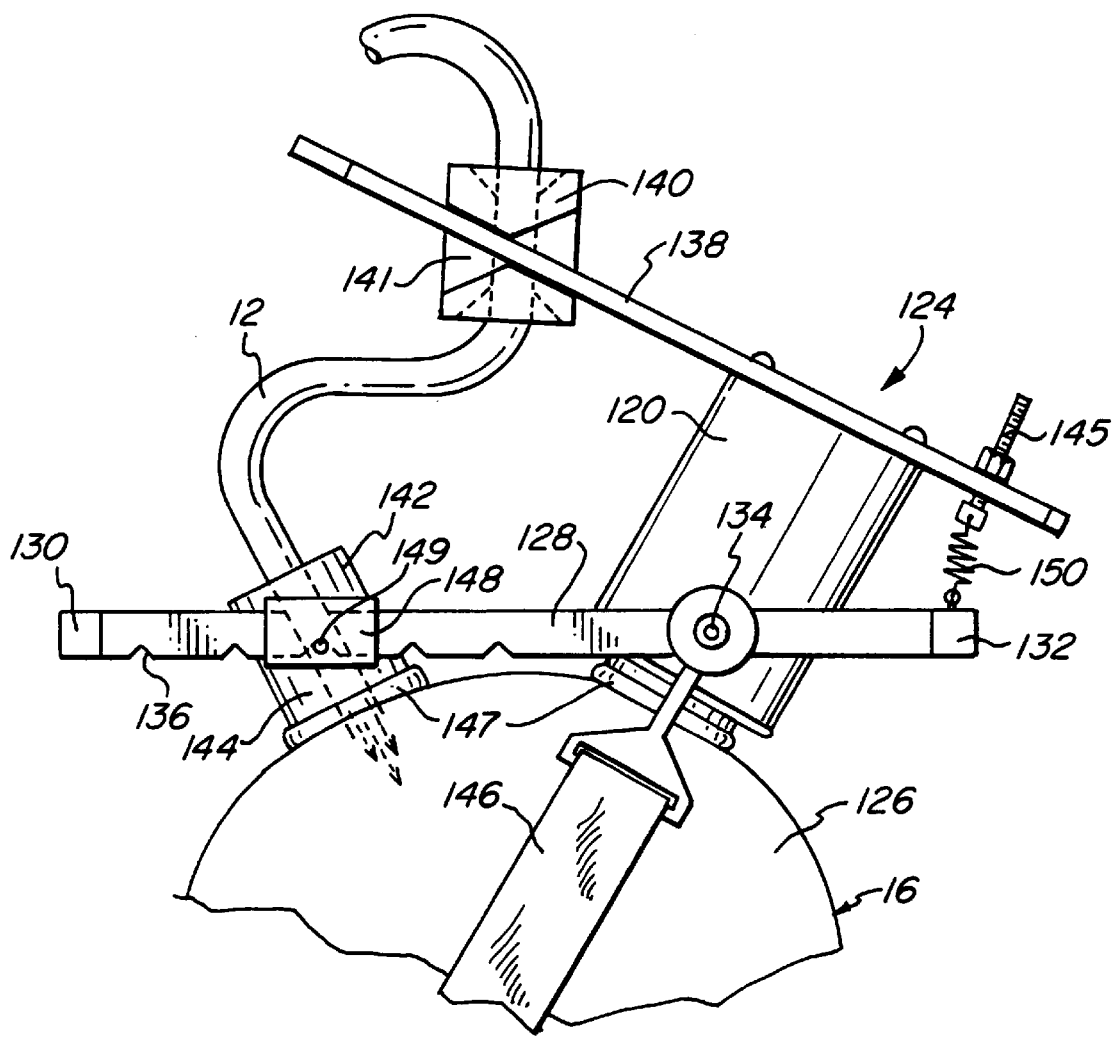
FIG. 2 is an apparatus for placing a light probe and a detector on a cranium.
Figure 3:
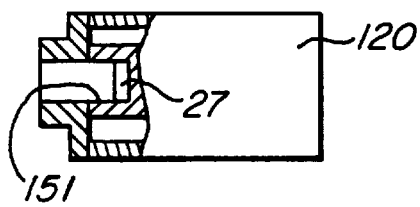
FIG. 3 is a cut-away cross section of a housing with a detector for use with the invention of FIG. 1.

Any suitable head-mounting apparatus for applying the probe and the detector or the input tip of a second fiber carrier to a test subject's cranium may be used. An example is a device 124 (FIG. 2) that positions the cylindrical housing 120 containing the detector 27 (FIG. 3) so that the detector housing rests directly against the skull 126. A pair of parallel, cantilevered arms 128 (one seen) are affixed apart by a pair of end struts 130, 132. The arms straddle the detector housing which supports a transverse axle 134 on which the arms rotate a short distance from one end strut 132. Along the long portion of the arms from the axle are a series of aligned notches 136 facing toward the subject's cranium 16. A plate 138 is attached to the outer end of the detector housing. A strain relief retainer 140 supports the input fiber carrier 12 passing through the plate, the retainer having angular slots 141 at the plate to allow flexibility in orientation. Another strain relief mount 142 for the light probe tip 144, with some slack in the fiber carrier between mounts, is attached to a rod 149 that can be positioned across the arms in a selected pair of notches. The rod is retained on the arms with a spring loaded detent clip 148 over each arm. An extension spring 150 is stretched between the plate 138 and the strut 132 that is on the opposite side of the axle 134 from the probe mount 142, with a threaded adjuster 145 for spring tension. An elastic strap 146 attached to the axle ends passes under the subject's chin to secure the device to the cranium, with the detector housing held against the cranium with the strap. The fiber probe tip 144 on the cantilever is urged against the skull by the extension spring. Disposable, pressure sensitive foam gaskets 147 mounted respectively on the detector housing and the probe mount allow conformity to the cranium and provide a barrier to stray light. Such a device allows adjustment of the spacing between the inlet probe and the detector, and provides a range of tilt angles to accommodate the natural curvature of the skull, while independently maintaining the probe and detector to the skull. For stability and convenience, the device should be suspended from overhead with a counterbalance to neutralize its weight.

To allow only the scattered light from a well-defined exit site on a brain to be collected, a light pipe 151 (FIG. 3) should be disposed in the entrance of the AP detector housing 120 between the detector surface and the cranium. This pipe, e.g. formed in an inside wall of the housing 120 as shown, should be polished (e.g. aluminum) and of minimal practical length such as 3 mm to position the face of the detector this distance above the cranium. Pipe diameter should be equal to or slightly less than the detector diameter, e.g. 5.9 mm for a 6 mm detector.

Other means for passing the radiation into and out of the cranium may be used. For example, the inlet probe and exit probe or detector may be held with external supports in place of a head bracket. In such a case optical fibers may not be necessary.

The present computer programming for control and computations may be effected with a conventional language such as "C++" or Visual Basic™ from Microsoft. Adaptations of the programming for the present invention from the descriptions and flow charts herein will readily be recognized and achieved by those skilled in the art. The flow chart illustrates method and means for carrying out the invention.

The system utilizes amplitude modulation of radiation having a plurality of discrete (narrow band) spectral wavelength components, advantageously with homodyne or heterodyne measurement of phase shifts. Such a system is disclosed in an article "Low-Cost Frequency-Domain Photon Migration Instrument for Tissue Spectroscopy, Oximetry, and Imaging" by Yunsong Yang, Hanli Liu, Xingde Li and Britton Chance, Opt. Eng. 36 (5) 1562–1569 (May 1997). A similar system is described in an article "A Homodyne Frequency-Domain Instrument—I&Q Phase Detection System" by H. Y. Ma, C. W. Du and B. Chance, Proc. SPIE 2979, 826–837 (1997). The portions of each of these articles that are relevant to a modulated laser system and its use for calculating phase shift are incorporated herein by reference. The present system is summarized below, with details being set forth in these references. Other aspects of the technology of these articles are replaced or modified by the improvements set forth herein.

A plurality of laser diodes 50 (FIG. 1) provide radiation with several discrete (narrow band) components of wavelength in the desired range (e.g. 700–1100 nm), for example 754, 786, 810 and 830 which are convenient wavelengths with diode model numbers LT031MD, LT027MD, LT017MD and LT015MD respectively from Sharpe Electronics, and 870 nm with Sanyo diode model number DL6033-101. The discrete wavelengths should be distributed across the desired range but need not correspond to the constituent peaks. The selected spectral range includes absorbance wavelengths of the selected constituents of interest, and the absorbance wavelength of at least one additional constituent in the organ that may interfere with those of interest that are selected. In a preferred aspect, the selected constituents comprise oxygenated hemoglobin and deoxygenated hemoglobin, in which case the additional constituents may comprise water, protein, lipid and perhaps one or more others, so that the total number of constituents is at least five. According to the present invention, the number of the plurality of discrete wavelengths (e.g. number of laser diodes) is at least equal to the total number of constituents.

An oscillator circuit 52 applies a continuous radio frequency (RF) signal 53 advantageously between about 100 MHz and 500 MHz, e.g. about 140 MHz, to each of the diodes to amplitude-modulate the emissions. The RF signal is passed through a time share switching circuit 54 controlled by the computer 34 to pass the RF signal sequentially to the diodes at a cycle rate of, for example, 10 Hz. Alternatively the modulation frequencies for the several diodes may have small frequency separations (e.g. 0.1 MHz) with omission of the switching circuit. Either of these or any other practical system may be used to provide separation of the signals for processing for the different wavelengths. The diode emissions are coupled into a beam or beams 12 of discrete radiation. The coupling may be achieved by combining fibers 56 from each diode into a total bundle 20. The combined beam is directed to the input positioning 16 on the cranium (or other organ). The output radiation 24, modified by the cranium is received by the radiation detector 27.

The detector signals are amplified through an amplifier 56 (which may be a series of amplifiers) and passed through a band pass filter 58 to remove noise outside of the selected radio frequency. Next, the phase shift and the amplitude of the detected signal may be determined, for example, by using a phase meter and dynode feedback as described in "A New Multi-Wavelength Phase Modulation System for Photon Diffusion Studies" by B. Guan, Y. Zhang, B. Chance, Proc. SPIE Vol. 2979 (1997) pp. 838–846.

In the present example, phase shift and amplitude are determined using an "in-phase and quadrature phase" (I&Q) demodulator circuit 60 that receives and compares signals from the detector with the base radio frequency signal 53 to provide outputs I(t) and Q(t) (where t is time) which are low-pass filtered by filters 62 into DC signals $I_{DC}$ and $Q_{DC}$ as described in Yang et al. These signals are A/D converted 32 and fed to the processor 36. Measured signal amplitude $A_m$ and phase $\theta_m$ are computed from the converted DC signals for each optical frequency utilizing equations set forth in Yang et al.:

$$\theta_m = \tan(Q_{DC}/I_{DC}) \qquad 1$$

$$A_m = (Q_{DC}^2 + I_{DC}^2)^{1/2} \qquad 2$$

As further set forth in the aforementioned articles, amplitude and phase are related to the absorption coefficient $\mu_a$ and the scattering coefficient $\mu_s$ by model equations (for an infinite, homogeneous medium):

$$\theta_m - \theta_O = r[(w^2 + v^2 \mu_a^2)^{1/2} - v\mu_a]^{1/2}/(2v/3\mu_s)^{1/2} \qquad 3$$

$$A_m/A_O = (3\mu_s/4\pi v r)\exp\{-r[(w^2+v^2\mu_a^2)^{1/2}+v\mu_a]^{1/2}/(2v/3\mu_s)^{1/2}\} \qquad 4$$

where $\theta_O$ is input phase of input radiation RF modulation, $A_O$ is amplitude of the input radiation to the organ, r is spacing between the organ input and output sites (FIG. 1), $w=2\pi f$ where f is the RF modulation frequency, and v is the speed of light in the organ. For speed of light, an accepted index of refraction of 1.4 for tissue may be used.

Figure 4:
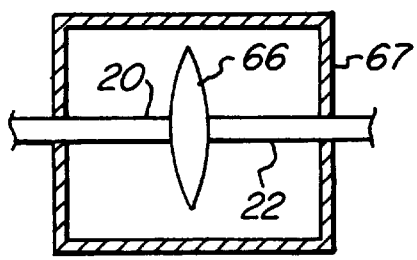
FIG. 4 is a cross sectional view of a housing with a filter for use with the invention of FIG. 1.

As indicated in Yang et al., with the scattering coefficient $\mu_s$ being unknown, Eqs. 3 and 4 may be solved iteratively for the absorption coefficient without determination of input values $\theta_O$ and $A_O$. Preferably, for greater accuracy, these values are determined by measurement of an amplitude $A_{nd}$ and phase $\theta_{nd}$ with a neutral density filter 66 (FIG. 4) positioned between the input fiber carrier 20 and the output carrier 22. The filter and fiber connections should be in an enclosure 67 to keep out stray light.

The input phase is equal to the measured phase, i.e. $\theta_O = \theta_{nd}$, and the input amplitude is $A_O = A_{nd}/t$ where t is the transmission efficiency of the filter. The filter has a predetermined optical density OD generally supplied by the manufacturer. $A_O$ and $\theta_O$ should be measured before each use (e.g. when the instrument is turned on) or more often depending on instrument stability.

Calculation of input amplitude is made with a form of the known Beer-Lambert law equation:

$$A_O = A_{nd}/10^{-(OD)} \qquad 5$$

With these determined values for input phase and amplitude, Eqs. 3 and 4 are solved simultaneously to compute the absorption coefficient $\mu_a$ (and scattering coefficient $\mu_s$ if desired). These determinations are made for each diode wavelength.

The absorption coefficient for each wavelength is related to concentrations of all of the relevant (selected and additional) constituents by a set of linear equations, one such equation being for each wavelength WL, relating absorption coefficient to concentrations of all of the constituents proportionately with respective extinction coefficients:

$$\mu_a^{WL} = E_1^{WL}C_1 + E_2^{WL}C_2 + E_3^{WL}C_3 + E_4^{WL}C_4 + E_5^{WL}C_5 + \mu_{ab}^{WL} \qquad 6$$

where C is concentration of a constituent, E is extinction coefficient, the numeral subscripts 1 through 5 represent the different constituents (collectively selected and additional), and $\mu_{ab}$ is a background absorption coefficient which may be determined separately by measurements with a direct connection of the input fiber carrier and the output carrier. The extinction coefficients are known from standard chemistry handbooks. The superscript WL refers to each of the five wavelengths, so that there are five such equations.

More broadly, the number of these linear equations is equal to or more than the total number of selected and additional constituents, each equation being for a wavelength. Thus the equations may be solved simultaneously by computer to obtain the desired concentrations of (for example) oxygenated hemoglobin (subscript 1) and deoxygenated hemoglobin (subscript 2); the additional constituents water, protein and lipid (subscripts 3, 4 and 5) need not be determined unless desired.

Figure 5:
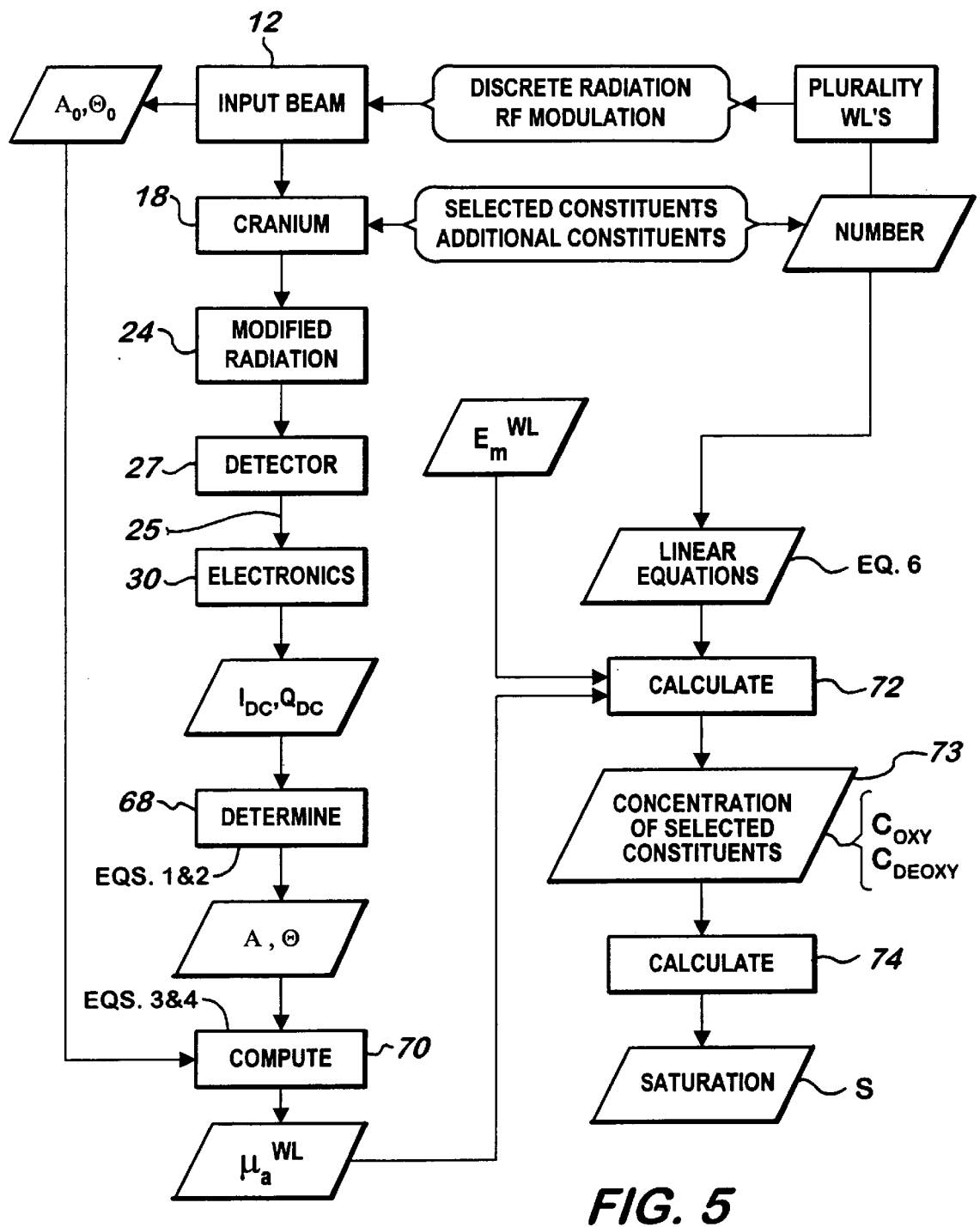
FIG. 5 is a first flow chart of computations performed in accordance with the invention.

The flow chart of FIG. 5 illustrates the procedures. An input beam 12 of discrete radiation is formed of a plurality of discrete wavelengths in an infrared spectral range that includes absorbance wavelengths of the selected constituents and at least one additional constituent in the organ. Each wavelength has a predetermined input amplitude $A_O$ and is modulated with a radio frequency signal having a predetermined input phase $\theta_O$. The selected constituents and the one or more additional constituents constitute a total number of constituents having significant absorbance in the spectral range, the plurality of wavelengths in number being at least equal to the total number of constituents.

The input beam 12 (also FIG. 1) is directed into an animal organ such as a brain 17 within a cranium 18 such that the radiation is modified by the selected and additional constituents, and a radiation detector 27 is positioned so as to be receptive of the modified radiation 24 from an exit site from the cranium so as to generate a corresponding output signal 25 for each wavelength. The output signal is converted electronically 30 (or by computer) to modified output signals ($I_{DC}$ and $Q_{DC}$). An output amplitude A and an output phase $\theta$ are determined 68 by computation from each modified output signal for each wavelength. An absorption coefficient $\mu_a^{WL}$ is computed 70 for each wavelength from the input amplitude $A_O$, the output amplitude A, the input phase $\theta_O$ and the output phase $\theta$, from Eqs. 3–4 relating phase and amplitude to absorption coefficient and scattering coefficient $\mu_s$. Concentration 73 of each of the selected constituents is calculated 72 from a plurality of simultaneous linear equations (Eq. 6) equal in number to the total number of constituents, each equation being for a different wavelength relating absorption coefficient to concentrations of all of the constituents proportionately with respective extinction coefficients $E_n^{WL}$. The preferable concentrations calculated are $C_{oxy}$ and $C_{deoxy}$ for oxygenated and deoxygenated hemoglobin respectively. If desired, the saturation $S = C_{oxy}/(C_{oxy}+C_{deoxy})$ may be calculated 74.

Figure 6:
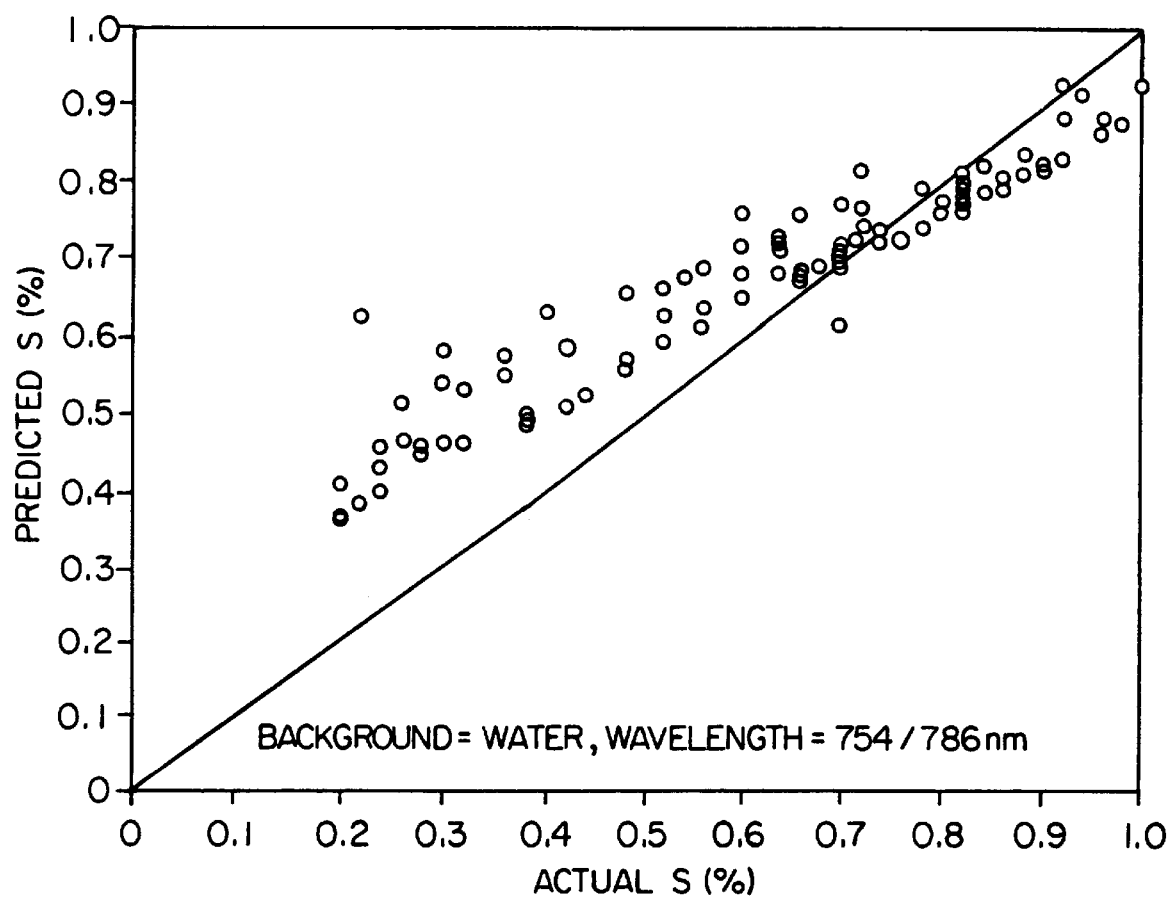
FIG. 6 is a plot of a set of predicted saturation values versus actual saturation values.

Simulation computations indicate that actual saturation of oxygen in hemoglobin may deviate from measured saturation, the latter being determined with frequency modulated radiation using two wavelengths as taught by Yang et al., or with apparatus such as depicted in FIG. 1 and associated procedures with five wavelengths. FIG. 6 shows measured (predicted) saturation to be too high for lower values, and too low for higher values. This is addressed below.

In an absorption relationship similar to Eq. 6 which assumes absorption by only certain constituents, a total absorption coefficient $\mu_a^\sim$ may be expressed more broadly as a weighted sum of significant absorptions:

$$\mu_a^\sim = F_w\mu_w + F_m\mu_m + F_b\mu_b \qquad 7$$

where $F_w$, $F_m$ and $F_b$ are volume fractions respectively of water, tissue matrix and blood, and $\mu_w, \mu_m$ and $\mu_b$ are specific absorption coefficients respectively for water, matrix and blood. There is a different Eq. 7 for each wavelength considered. Two of the three components of the equation are further subdivided for constituents of the tissue matrix and blood, as follows:

$$F_m\mu_m = F_{ml}\mu_l + F_{mp}\mu_p \qquad 8$$

where $F_{ml}$ and $F_{mp}$ are volume fractions respectively of lipid and matrix protein, and $\mu_l$ and $\mu_p$ are absorption coefficients respectively for lipid and protein; and $$F_b\mu_b = H\{F_{rw}\mu_w + F_{rl}\mu_l + F_{rp}[(1-S)\mu_{Hb} + S\mu_{Hbo}]\} + (1-H)\{F_{wP}\mu_w + F_{lP}\mu_l + F_{pP}\mu_p\} \quad 9$$

where H is hematocrit (volume fraction of red blood cells (RBC) in the blood); S is blood oxygen saturation (ratio of oxy-hemoglobin to total hemoglobin); $F_{wR}$, $F_{lR}$ and $F_{pR}$ are volume fractions respectively of water, lipid, and protein in red blood cells; $F_{wP}$, $F_{lP}$ and $F_{pP}$ are volume fractions respectively of water, lipid and protein in plasma; and $\mu_{Hb}$ and $\mu_{HbO}$ are absorption coefficients respectively for deoxygenated and oxygenated hemoglobin.

Figure 7:
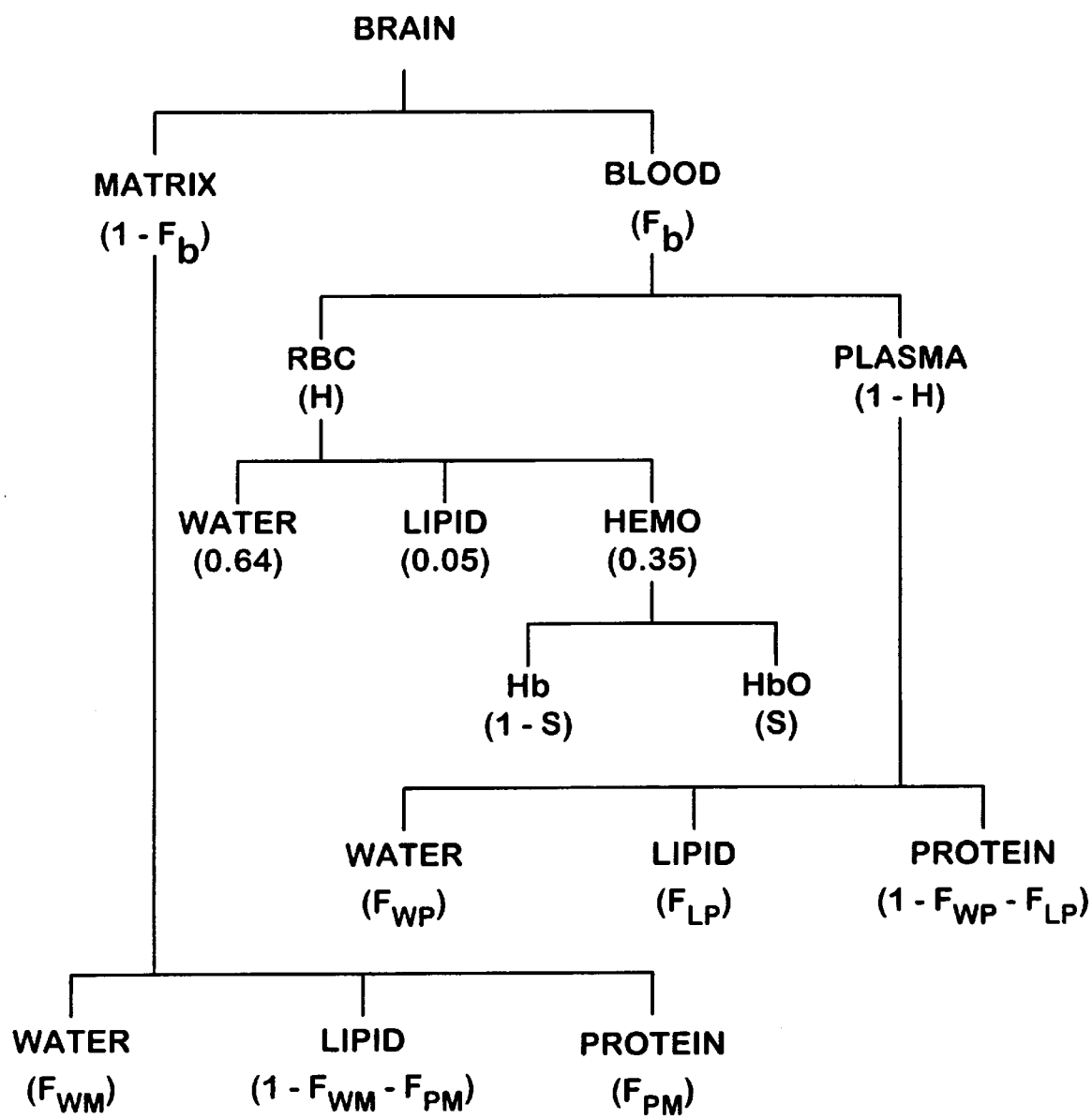
FIG. 7 is a diagram of the constituents of brain tissue.

The breakdown of constituents and associated volume fractions (in percent) is shown in FIG. 7, with ranges of the volume fractions given in Table 1, wherein $F_{wm}$ and $F_{pm}$ are volume fractions respectively of water and protein in tissue matrix.

TABLE 1

| | | |
|---|---|---|
| S | Saturation | 20–100% |
| H | Hematocrit | 30–50% |
| $F_b$ | Blood in Matrix | 3–5% |
| $F_{wP}$ | Water in Plasma | 91–94% |
| $F_{lP}$ | Lipid in Plasma | 0.5–1.5% |
| $F_{wm}$ | Water in Matrix | 70–85% |
| $F_{pm}$ | Protein in Matrix | 8–12% |

Figure 8:
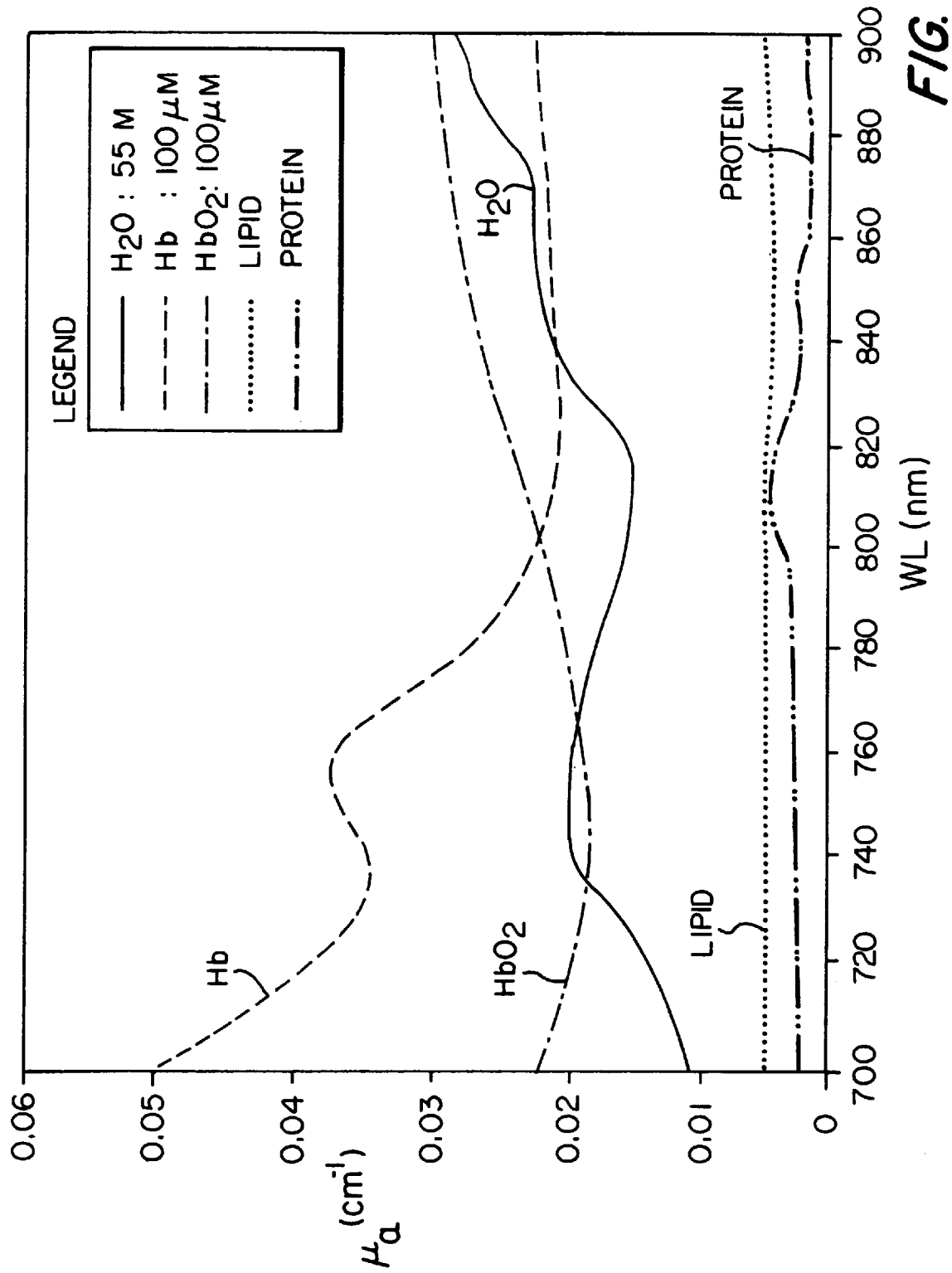
FIG. 8 is a plot of absorption coefficient as function of wavelength for various constituents.
Figure 9:
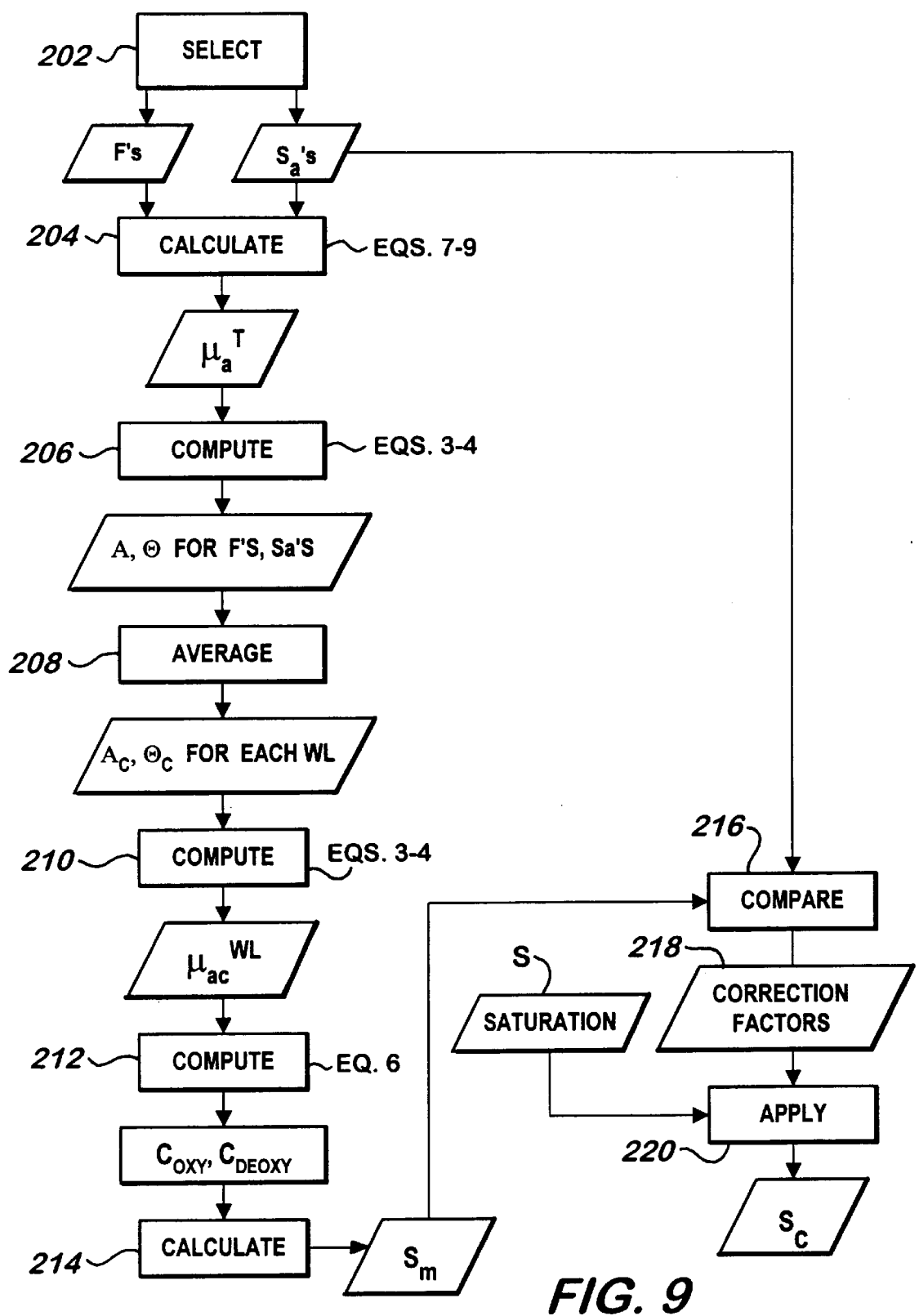
FIG. 9 is a second flow chart of computations performed in accordance with the invention.

Thus the absorption coefficient for the brain is a sum of contributions from fundamental biochemical constituents whose individual absorption coefficients are well known for each wavelength (FIG. 8). The foregoing model is set forth in "Frequency Domain Reflectance for the Determination of the Scattering Absorption Properties of Tissue" by M. S. Patterson, J. D. Moultin, B. C. Wilson, K. W. Berndt and J. R. Lakowicz, J. Appl. Optics, vol. 30, 4474 (1991). Typical volume ranges for tissue constituents are also published.

According to an aspect of the present invention, a computer simulation is effected by varying the volume fractions F and "actual" oxygen saturation $S_a$. Sets of values for the fractions are selected 202, preferably randomly by computer without operator input to simulate random populations. For later comparison, the selected ("actual") saturation values are stored ($S_a$). A set of absorption coefficients for the spectral range are calculated 204 from Eqs. 7–9 for each set of fractions and saturations for each wavelength.

Amplitude ratio and phase shift are computed 206 by some statistical technique, for example, Monte-Carlo Simulation "A Monte-Carlo Method for the Absorption and Flux Distribution of Light In Tissue" by B. C. Wilson and G. Adam, Med. Phys. 10 (6), 824 (November/December 1983). The computations use the simulation-generated total absorption coefficients $\mu_a^\sim$ for each wavelength used in actual measurements, with the same RF modulation frequency as in actual measurements. The computed ratio and shift are averaged 208 for each wavelength yielding $A_c$ and $\theta_c$. These are treated as having been measured, and are utilized in Eqs. 3–4 to re-compute 210 absorption coefficient $\mu_{ac}^{WL}$ for each wavelength. The equations may be numerically solved simultaneously in a normal manner, such as with input amplitude $A_O$ and phase $\theta_O$ previously determined and stored from neutral density filter measurements as taught herein, or as taught, for example, by Yang et al., Patterson et al. or in an article "Semi-infinite-geometry Boundary Problem for Light Migration in Highly Scattering Media: A Frequency-domain Study in the Diffusion Approximation", by S. Fantini, M. A. Francerchini and E. Grafton, J. Opt. Soc. Am. 11, #10, 2128 (October 1994).

The recomputed $\mu_{ac}^{WL}$ is then used in the simultaneous linear equations Eq. 6 to compute 212 hemoglobin concentrations, from which "measured" (simulated) saturation $S_m$ is calculated 214. Alternatively, the simulation-generated absorption coefficients $\mu_a^\sim$ may be used directly in the equations Eq. 6, although recomputed values are preferable. A recomputation of the absorption coefficient is particularly beneficial when the number of wavelengths is less than the total number of constituents including additional, interfering constituents.

The "measured" saturation $S_m$ and "actual" saturation $S_a$ are compared 216 by fitting them to a curve (linear should be sufficient) to obtain correction factors 218, e.g. slope m and offset o in $S_a = mA_m + o$ for each wavelength. These factors, or more broadly one or more such correction factors, are stored and applied 220 through reverse of this equation to real measured saturation data S (FIG. 5) to obtain corrected saturation $S_c$ for oxygen.

Figure 10:
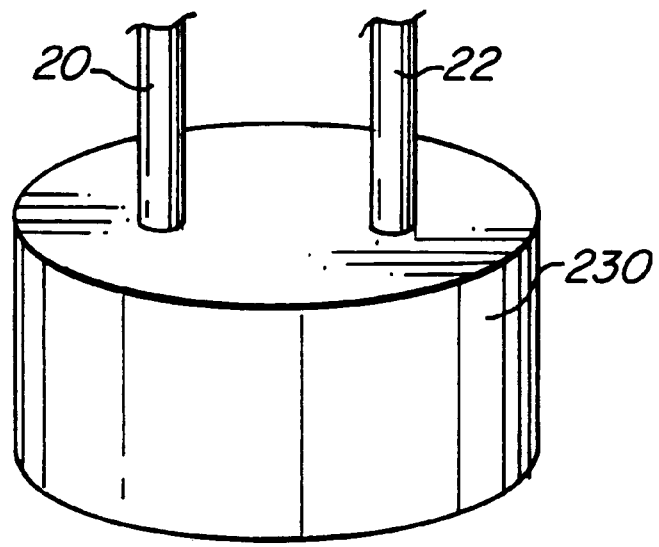
FIG. 10 is a perspective of a "phantom" organ for use with the invention of FIG. 1.

Errors are introduced from the choice of imperfect models including Eqs. 3–4 being for an infinite, homogeneous case which do not fully reflect actual circumstances. A calibration may be effected for a correction to the phase $\theta_m$ and amplitude $A_m$ calculated from these equations. In a further aspect, to achieve such corrections, at least one standardized medium is provided as a "phantom" organ 230 (FIG. 10), preferably at least two such organs. The organs may be shaped like a cranium. Also provided is a standard sample of each of the selected and additional constituents, e.g. oxygenated hemoglobin, deoxygenated hemoglobin, water, protein and lipid, all with predetermined (known) concentrations and extinction coefficients.

The standardized media are made of a non-absorbing material (nil absorption coefficient), for example, of a clear non-absorbing resin, e.g. epoxy, that contain scattering particles such as intralipid of size between about 0.2 and 1.0 $\mu$m, and have predetermined (known) scattering coefficients. Such phantoms are taught in articles "A Design for a Stable and Reproducible Phantom for Use in Near-infrared Imaging and Spectroscopy" by M. Firbank and D. T. Delpy, Physics in Medicine and Biology 38, pp 847–853 and An Improved Design for a Stable and Reproducible Phantom for Use in Near-infrared Spectroscopy and Imaging" by M. Firbank, M. Oda and D. T. Delpy, Physics in Medicine and Biology 40, pp 955–961. The portions of these articles relevant to the formation of phantom organs are incorporated herein by reference. At least two phantoms with different scattering coefficients should be used to provide a range of measured phases.

Figure 11:
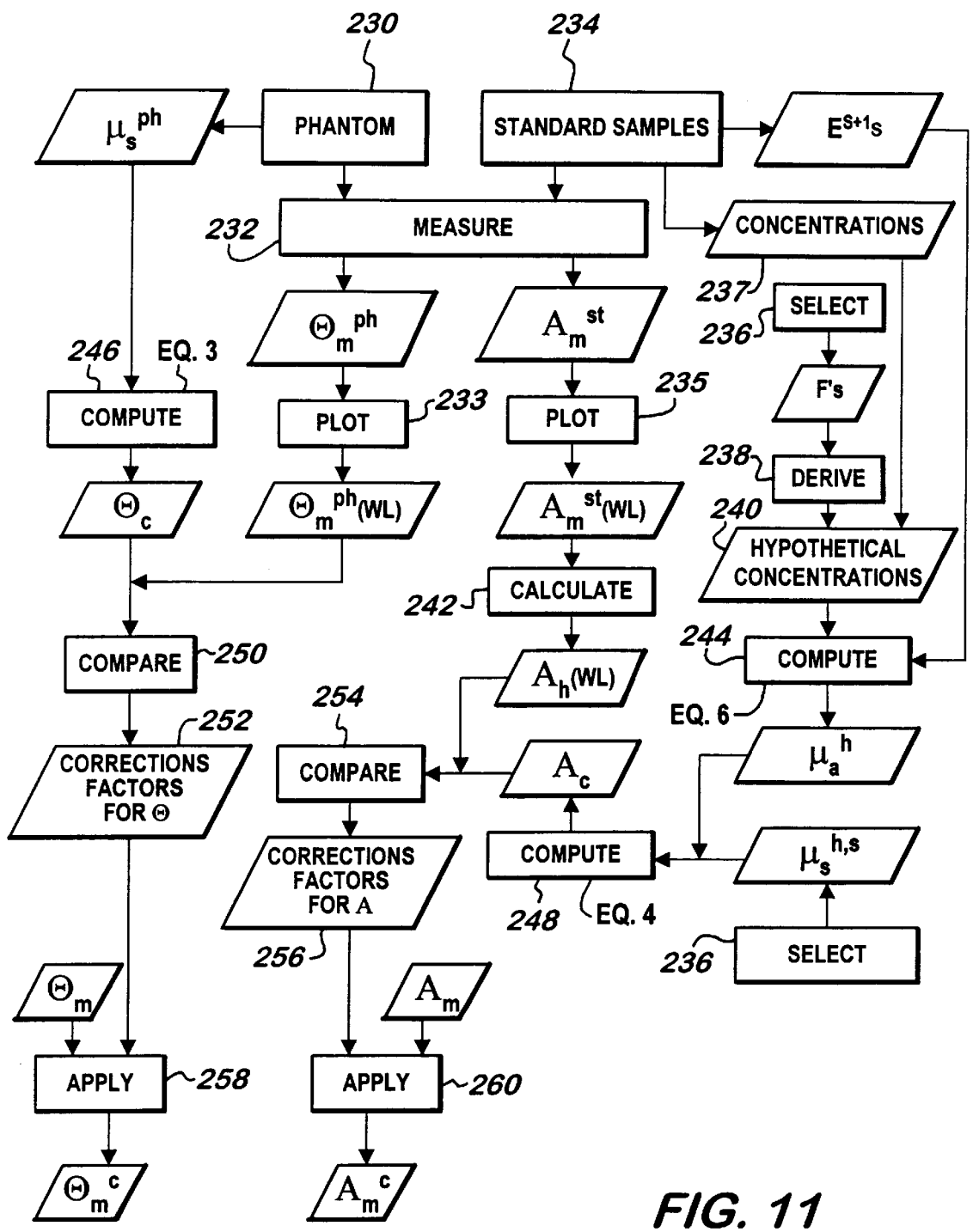
FIG. 11 is a third flow chart of computations performed in accordance with the invention.

With each phantom organ 230, the input carrier 20 and the output carrier 22 are abutted to the phantom to simulate passing of radiation through an actual organ. Any terminal device that is used to couple the carriers to an actual organ should be used (none shown in FIG. 10). With an input beam of RF modulated, discrete radiation from the instrument, phase $\theta_m^{ph}$ is measured 232 (FIG. 11) for the phantoms using Eq. 1 and the procedures described with respect to FIG. 5. If desired for wavelengths other than those utilized, the values may be fitted or interpolated and extrapolated from the discrete wavelengths to provide a plot 233 of measured phase $\theta_m^{ph}(WL)$ vs. wavelength, for each of the known scattering coefficients $\mu_s^{ph}$ for the phantoms. In any event, phase is determined for various wavelengths.

Figure 12:
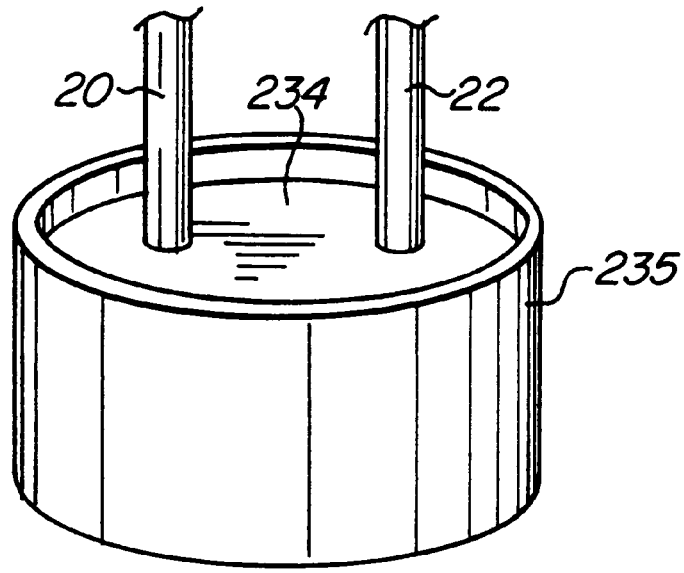
FIG. 12 is a perspective of a sample container for use with the invention of FIG. 1.

The carriers 20, 22 are inserted similarly into each of the standard samples 234 held in a container 235 (FIG. 12). Amplitudes $A_m^{st}$ are measured 232 for the standard samples using Eq. 2 and the procedures described with respect to FIG. 5. There is no significant scattering, so scattering coefficient and phase shift are zero. (In this case $I_{DC}$ (FIG. 1) is a direct measure of $A_m^{st}$.) If desired, the amplitudes are similarly fitted or interpolated and extrapolated from the discrete wavelengths to provide a plot 235 of measured amplitude $A_m^{st}$(WL) vs. wavelength. (The wavelength fitting alternatively may be effected after any the following steps relating to computed amplitude.) Various scattering coefficients $\mu_s^h$ and volume fractions F in simulated mixtures of all constituents are selected 236, preferably randomly by computer. From the fractions and the predetermined concentrations 237, a set of hypothetical concentrations 240 of mixtures for hypothetical "organs" are derived 238 with the aid of FIG. 7 and Table 1. There should be a significant number of hypothetical organs, i.e. at least five, e.g. 20, for each wavelength. Hypothetical ("measured") amplitudes $A^h$ for the hypothetical organs are calculated 242 for the various wavelengths, using the fact that the amplitudes are proportional to the concentrations C for all constituents. With the known extinction coefficients $E^{st}$, hypothetical absorption coefficients $\mu_a^h$ are computed 244 for the hypothetical organs with Eq. 6. To the extent that there is more than one hypothetical value for amplitude (or absorption coefficient) for a wavelength, such values are averaged.

Next, computations are made with the model equations for each wavelength. Phases $\theta_c$ are computed 246 with Eq. 3 from the known scattering coefficients $\mu_s^{ph}$ for the phantoms where there is no absorption ($\mu_a=0$). Amplitudes $A_c$ are computed 248 with Eq. 4 from the calculated absorption coefficients $\mu_a^h$ and the randomly selected scattering coefficients $\mu_s^h$. The other parameters in these equations are known as presented above.

For each wavelength, the measured phases $\theta_m^{ph}$ and computed phases $\theta_c$ are compared 250, as by a regression analysis, to effect phase calibration factors 252, e.g. in the form of a slope and bias for each wavelength. Similarly, the hypothetical ("measured") amplitudes $A_h$ and computed amplitudes $A_c$ are compared 254 to effect amplitude calibration factors 256, e.g. in the form of a slope and bias, again for each wavelength. These calibration factors are advantageously generated initially (e.g. at the factory) and are stored. Each measured phase $\theta_m$ and amplitude $A_m$ determined for actual organs from Eqs. 1–2 are then corrected (calibrated) to $\theta_m^c$ and $A_m^c$ by respective application 258, 260 of the factors, for subsequent use in Eqs. 3–4.

Figure 13:
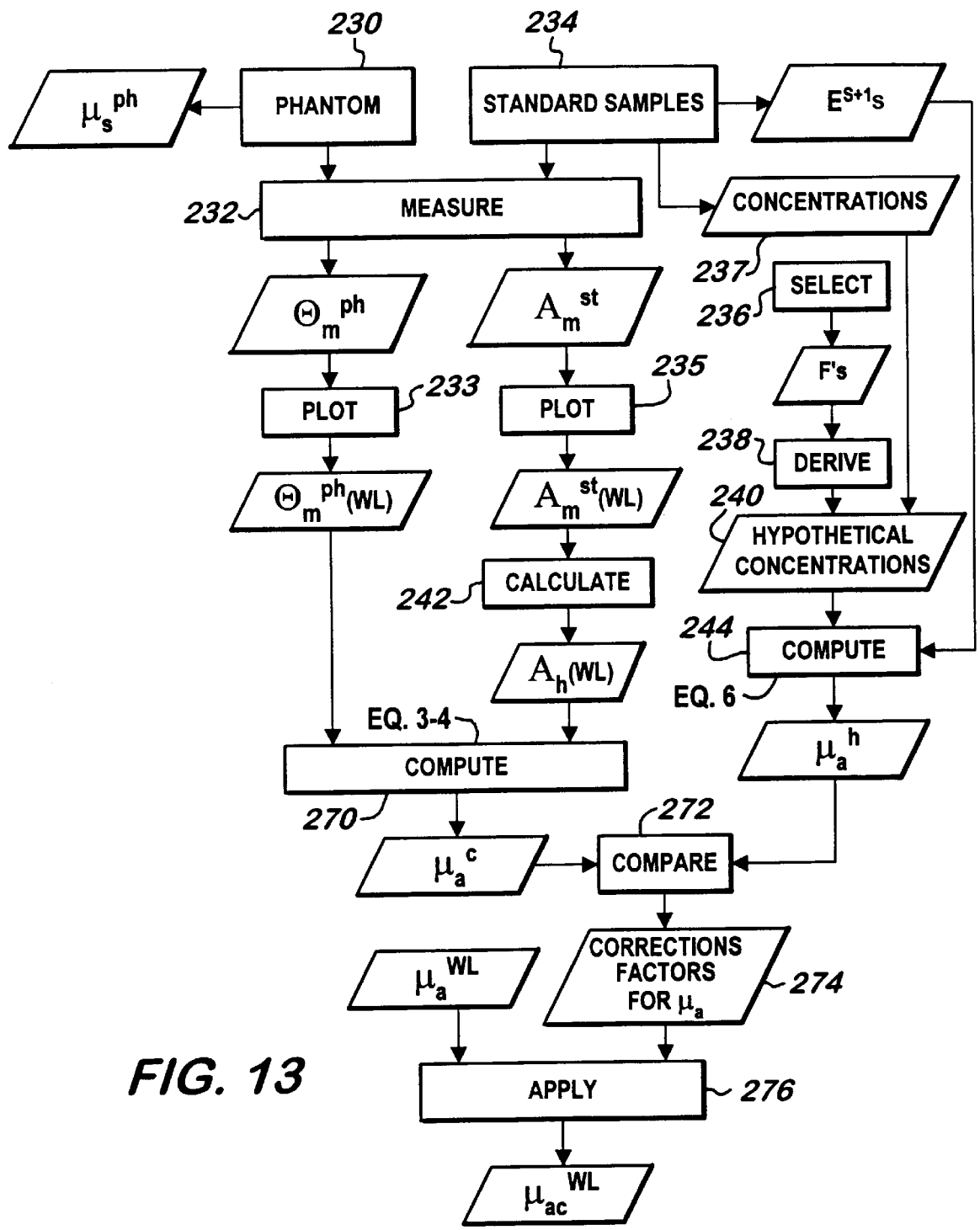
FIG. 13 is a fourth flow chart of computations performed in accordance with the invention.

An alternative approach, which replaces computations and comparisons of phases and amplitudes, is to compute and compare absorption coefficients (FIG. 13). As described above with respect to FIG. 11, measurements with the phantom and standard samples and associated calculations are used to generate "measured" phase vs. wavelength $\theta_m^{ph}$(WL) and "measured" amplitude vs. wavelength $A_h$(WL). Also, hypothetical absorption coefficients $\mu_a^h$ are computed from selected volume fractions F.

For each wavelength the "measured" phase $\theta_m^{ph}$(WL) and amplitude $A_h$(WL) (or averages of multiple values for the wavelength) are used in the model Eqs. 3–4 to compute 270 absorption coefficient $\mu_a^c$. This coefficient is compared 272 with the hypothetical absorption coefficients $\mu_a^h$, as by a regression analysis, to effect phase calibration factors 274, e.g. in the form of a slope and bias for each wavelength which are stored. The measured absorption coefficients $\mu_a^{WL}$, that are determined 68 and computed 70 (FIG. 5) through Eqs. 1–4 for actual organs, are then corrected (calibrated) to $\mu_{ac}^{WL}$ by application 276 of the factors. This calibrated coefficient is subsequently used in the calculation 72 for concentrations 73 and, if desired, saturation S.

It will be appreciated that equations utilized herein are based on published matter, and that such equations may be modified or replaced with other known relationships or upon further studies. Therefore, other equations that reasonably relate the relevant variables may be used in the procedures set forth herein, and should be deemed equivalent for the purposes of this invention.

While the invention has been described above in detail with reference to specific embodiments, various changes and modifications which fall within the spirit of the invention and scope of the appended claims will become apparent to those skilled in this art. Therefore, the invention is intended only to be limited by the appended claims or their equivalents.

What is claimed is:

1. A method of monitoring one or more selected constituents in an animal organ with a spectrometric instrument that includes a source of an input beam of discrete radiation formed of a plurality of discrete wavelengths in an infrared spectral range that includes absorbance wavelengths of the selected constituents and one or more additional constituents in the organ, wherein each wavelength has a predetermined input amplitude and is modulated with a radio frequency signal having a predetermined input phase, and the instrument further includes a radiation detector receptive of such radiation to generate representative signal data, wherein the selected constituents and the additional constituents constitute a total number of constituents having significant absorbance in the spectral range, the plurality of wavelengths is at least equal in number to the total number of constituents, and the method comprises steps of:

directing the input beam into an animal organ such that the radiation is modified by the constituents, and positioning the radiation detector so as to be receptive of the modified radiation from an exit site from the organ so as to generate a corresponding output signal for each wavelength;

determining from each output signal an output amplitude and an output phase for each wavelength;

computing an absorption coefficient for each wavelength from the input amplitude, the output amplitude, the input phase and the output phase, with respective equations relating phase, amplitude, absorption coefficient and scattering coefficient; and calculating concentration of each of the selected constituents from a plurality of simultaneous equations at least equal to the total number of constituents, each equation being for a different wavelength relating absorption coefficient to concentrations of all of the constituents proportionately with respective predetermined extinction coefficients.

2. The method of claim 1 wherein the selected constituents comprise oxygenated hemoglobin and deoxygenated hemoglobin, and the additional constituents comprise water, protein and lipid, whereby the total number of constituents is at least five.

3. The method of claim 2 wherein the selected constituents further comprise cytochrome oxidase.

4. The method of claim 1 wherein the respective equations comprise Eqs. 3 and 4 as defined in the specification.

5. The method of claim 1 wherein the simultaneous equations comprise Eq. 6 as defined in the specification.

6. The method of claim 1 wherein, to predetermine each input amplitude and input phase, the method further comprises passing the input beam through a neutral density filter to the radiation detector so as to generate a corresponding reference signal for each wavelength, the filter having a predetermined optical density;

determining from each reference signal a reference amplitude and a reference phase for each wavelength, whereby the input phase is equal to the reference phase; and calculating the input amplitude from the reference amplitude and the optical density.

7. The method of claim 6 wherein the input amplitude is calculated from Eq. 5 as defined in the specification.

8. The method of claim 1 wherein the organ comprises blood containing oxygenated hemoglobin and deoxygenated hemoglobin, and the method further comprises calculating a measured oxygen saturation in the blood as a ratio of concentration of oxygenated hemoglobin to a total of concentrations of oxygenated hemoglobin and deoxygenated hemoglobin.

9. The method of claim 8 wherein the organ further comprises water and tissue matrix, and the method further comprises steps of:

providing an absorption relationship relating total absorption coefficient for the organ to oxygen saturation, specific absorption coefficients and volume fractions respectively for water, tissue matrix, blood, and for constituents of the tissue matrix and the blood, wherein the specific absorption coefficients are predetermined for each wavelength, and the volume fractions can vary;

selecting at least one set of values for the oxygen saturation and the volume fractions, and, for each set, calculating therefrom and from the specific absorption coefficients a corresponding calculated organ absorption coefficient for a selected wavelength;

utilizing the calculated organ absorption coefficients for computing concentrations of oxygenated hemoglobin and deoxygenated hemoglobin from the plurality of simultaneous equations, and further calculating oxygen saturations from the concentrations; and comparing the calculated oxygen saturations to the selected values for oxygen saturation to obtain a correction factor, and storing the correction factor for application to the measured oxygen saturation to obtain a corrected oxygen saturation.

10. The method of claim 9 wherein the step of utilizing comprises computing an output amplitude and an output phase from the calculated organ absorption coefficients using the respective equations relating phase and amplitude to absorption coefficient, computing from the respective equations a recomputed absorption coefficient from the computed output amplitude and the computed output phase, and utilizing the recomputed absorption coefficient for calculating concentrations of oxygenated hemoglobin and deoxygenated hemoglobin from the plurality of simultaneous equations.

11. The method of claim 1 further comprising steps of:

providing at least one standardized medium of a non-absorbing material containing scattering matter with a predetermined scattering coefficient and nil absorption coefficient, and further providing standard samples of the selected and additional constituents, the standard samples having predetermined concentrations and predetermined extinction coefficients;

directing the input beam into the medium such that the radiation is modified by the medium, positioning the detector to be receptive of such modified radiation so as to generate an output signal for the medium, and determining from each output signal a measured phase for the medium for each wavelength;

computing from the predetermined scattering coefficient a computed phase for each wavelength from a model equation relating phase to scattering coefficient;

directing the input beam into each standard sample such that the radiation is modified by the sample, positioning the detector so as to be receptive of such modified radiation so as to generate an output signal for each sample, and determining from each output signal a measured amplitude for each sample for selected wavelengths;

deriving a set of hypothetical concentrations of the constituents for hypothetical organs, computing therefrom and from the predetermined concentrations a hypothetical absorption coefficient for each wavelength from an absorption equation relating absorption coefficient to concentrations and extinction coefficients, selecting a set of hypothetical scattering coefficients, and computing from the hypothetical absorption coefficient and the selected scattering coefficients a computed amplitude for each wavelength from a model equation relating amplitude to absorption coefficient and scattering coefficient;

comparing the measured phase to the computed phase for each wavelength to effect phase calibration factors, comparing the measured amplitude to the computed amplitude for each wavelength to effect amplitude calibration factors, and storing the calibration factors for application respectively to output phase and output amplitude computed from signal data for an animal organ.

12. The method of claim 1 further comprising steps of:

providing at least one standardized medium of a non-absorbing material containing scattering matter with a predetermined scattering coefficient and nil absorption coefficient, and further providing standard samples of the selected and additional constituents, the standard samples having predetermined concentrations and predetermined extinction coefficients;

directing the input beam into the medium such that the radiation is modified by the medium, positioning the detector to be receptive of such modified radiation so as to generate an output signal for the medium, and determining from each output signal a measured phase for the medium for each wavelength;

directing the input beam into each standard sample such that the radiation is modified by the sample, positioning the detector so as to be receptive of such modified radiation so as to generate an output signal for each sample, and determining from each output signal a measured amplitude for each sample for selected wavelengths;

deriving a set of hypothetical concentrations of the constituents for hypothetical organs, computing therefrom and from the predetermined concentrations a hypothetical absorption coefficient for each wavelength from an absorption equation relating absorption coefficient to concentrations and extinction coefficients;

computing from the measured phase and the measured amplitude a computed absorption coefficient from for each wavelength from the model equations relating phase, amplitude, absorption coefficient and scattering coefficient; and comparing the computed absorption coefficient and the hypothetical absorption coefficient for each wavelength to effect coefficient calibration factors, and storing the calibration factors for application to measured absorption coefficients computed from signal data for an animal organ, to effect corrected absorption coefficients for subsequent calculation of concentrations.

13. A method of determining a correction factor for measured blood saturation in an animal organ, the saturation being measured with a spectrometric instrument that includes a source of an input beam of discrete radiation formed of a plurality of discrete wavelengths in an infrared spectral range that includes absorbance wavelengths of blood hemoglobin in the organ, the hemoglobin comprising oxygenated hemoglobin and deoxygenated hemoglobin, and the blood saturation being a ratio of oxygenated hemoglobin to a total of oxygenated hemoglobin and deoxygenated hemoglobin, wherein:

each wavelength has a predetermined input amplitude and is modulated with a radio frequency signal having a predetermined input phase, and the instrument further includes a radiation detector receptive of such radiation to generate representative signal data;

the input beam is directed into an animal organ such that the radiation is modified by the hemoglobin, and the radiation detector is positioned so as to be receptive of the modified radiation from an exit site from the organ so as to generate a corresponding output signal for each wavelength;

an output amplitude and an output phase for each wavelength are determined from each output signal;

an absorption coefficient is computed for each wavelength from the input amplitude, the output amplitude, the input phase and the output phase, from respective equations relating phase and amplitude to absorption coefficient and scattering coefficient;

concentrations of oxygenated hemoglobin and deoxygenated hemoglobin are calculated from a pair of simultaneous linear equations, each equation being for a different wavelength relating absorption coefficient to the concentrations proportionately with respective predetermined extinction coefficients; and a measured oxygen saturation in the blood is calculated; and the method comprises steps of:

providing an absorption relationship relating absorption coefficient for the organ to oxygen saturation, specific absorption coefficients and volume fractions respectively for water, tissue matrix, blood, and for constituents of the tissue matrix and the blood, wherein the specific absorption coefficients are predetermined for each wavelength, and the volume fractions can vary within predetermined ranges;

selecting at least one set of values for the oxygen saturation and the volume fractions, and, for each set, calculating therefrom a corresponding organ absorption coefficient for each wavelength;

utilizing the calculated organ absorption coefficients for calculating concentrations of oxygenated hemoglobin and deoxygenated hemoglobin from the plurality of simultaneous linear equations, and further calculating oxygen saturations from the concentrations; and comparing the calculated oxygen saturations to the selected values for oxygen saturation to obtain one or more correction factors, and storing the correction factors for application to the measured oxygen saturation to obtain a corrected oxygen saturation.

14. The method of claim 13 wherein the step of utilizing comprises computing a computed output amplitude and a computed output phase from the calculated organ absorption coefficients using the respective equations relating phase and amplitude to absorption coefficient, computing from the respective equations a recomputed absorption coefficient from the computed output amplitude and the computed output phase, and utilizing the recomputed absorption coefficient for calculating concentrations of oxygenated hemoglobin and deoxygenated hemoglobin from the plurality of simultaneous equations.

15. An apparatus for monitoring one or more selected constituents in an animal organ, comprising:

a spectrometric instrument comprising a source of an input beam of discrete radiation formed of a plurality of discrete wavelengths in an infrared spectral range that includes absorbance wavelengths of the selected constituents and one or more additional constituents in the organ, wherein each wavelength has a predetermined input amplitude and is modulated with a radio frequency signal having a predetermined input phase, and the instrument further comprises a radiation detector receptive of such radiation to generate representative signal data, wherein the selected constituents and the additional constituents constitute a total number of constituents having significant absorbance in the spectral range, the plurality of wavelengths is at least equal in number to the total number of constituents;

means for directing the input beam into an animal organ such that the radiation is modified by the constituents;

means for positioning the radiation detector so as to be receptive of the modified radiation from an exit site from the organ so as to generate a corresponding output signal for each wavelength;

means for determining from each output signal an output amplitude and an output phase for each wavelength;

means for computing an absorption coefficient for each wavelength from the input amplitude, the output amplitude, the input phase and the output phase, with respective equations relating phase, amplitude, absorption coefficient and scattering coefficient; and means for calculating concentration of each of the selected constituents from a plurality of simultaneous equations at least equal to the total number of constituents, each equation being for a different wavelength and relating absorption coefficient to concentrations of all of the constituents proportionately with respective predetermined extinction coefficients.

16. The apparatus of claim 15 wherein, to predetermine each input amplitude and input phase, the apparatus further comprises means for passing the input beam through a neutral density filter to the radiation detector so as to generate a corresponding reference signal for each wavelength, the filter having a predetermined optical density;

means for determining from each reference signal a reference amplitude and a reference phase for each wavelength, whereby the input phase is equal to the reference phase; and means for calculating the input amplitude from the reference amplitude and the optical density.

17. The apparatus of claim 15 wherein the organ comprises blood containing oxygenated hemoglobin and deoxygenated hemoglobin, and the apparatus further comprises means for calculating a measured oxygen saturation in the blood as a ratio of concentration of oxygenated hemoglobin to a total of concentrations of oxygenated hemoglobin and deoxygenated hemoglobin.

18. The apparatus of claim 17 wherein the organ further comprises water and tissue matrix, and the apparatus further comprises:
- a computer-stored absorption relationship relating total absorption coefficient for the organ to oxygen saturation, specific absorption coefficients and volume fractions respectively for water, tissue matrix, blood, and for constituents of the tissue matrix and the blood, wherein the specific absorption coefficients are predetermined for each wavelength, and the volume fractions can vary;
- means for selecting at least one set of values for the oxygen saturation and the volume fractions, and, for each set, means for calculating therefrom and from the specific absorption coefficients a corresponding calculated organ absorption coefficient for a selected wavelength;
- means for utilizing the calculated organ absorption coefficients to compute concentrations of oxygenated hemoglobin and deoxygenated hemoglobin from the plurality of simultaneous equations, and means for further calculating oxygen saturations from the concentrations; and
- means for comparing the calculated oxygen saturations to the selected values for oxygen saturation to obtain a correction factor, and means for storing the correction factor for application to the measured oxygen saturation to obtain a corrected oxygen saturation.

19. The apparatus of claim 18 wherein the means for utilizing comprises means for computing an output amplitude and an output phase from the calculated organ absorption coefficients using the respective equations relating phase and amplitude to absorption coefficient, means for computing from the respective equations a recomputed absorption coefficient from the computed output amplitude and the computed output phase, and means for utilizing the recomputed absorption coefficient to calculate concentrations of oxygenated hemoglobin and deoxygenated hemoglobin from the plurality of simultaneous equations.

* * * * *